United States Patent
Hughes et al.

(10) Patent No.: US 6,510,199 B1
(45) Date of Patent: Jan. 21, 2003

(54) METHOD AND SYSTEM FOR PROVIDING RADIATION TREATMENT TO A PATIENT (75) Inventors: John Hughes, Martinez, CA (US); Dennis Falkenstein, Danville, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 8 days.

(21) Appl. No.: 09/897,223

(22) Filed: Jul. 2, 2001

(51) Int. Cl.[7] .............................................. A61N 5/10
(52) U.S. Cl. .......................................... 378/65; 378/64
(58) Field of Search ..................................... 378/64, 65

(56) References Cited

U.S. PATENT DOCUMENTS

| 5,754,622 | A | | 5/1998 | Hughes | 378/65 |
| 5,970,499 | A | * | 10/1999 | Smith et al. | 707/102 |
| 6,052,435 | A | | 4/2000 | Hernandez-Guerra | 378/150 |
| 6,118,847 | A | | 9/2000 | Hernandez-Guerra | 378/65 |
| 6,253,210 | B1 | * | 6/2001 | Smith et al. | 707/102 |
| 6,381,576 | B1 | * | 4/2002 | Gilbert | 600/300 |
| 2001/0029509 | A1 | * | 10/2001 | Smith et al. | 707/104.1 |
| 2001/0048027 | A1 | * | 12/2001 | Walsh | 235/385 |
| 2002/0052875 | A1 | * | 5/2002 | Smith et al. | 707/10 |
| 2002/0087358 | A1 | * | 7/2002 | Gilbert | 705/2 |

* cited by examiner

*Primary Examiner*—David V. Bruce (57) ABSTRACT

A method and system for providing a radiation treatment to a patient utilizing a radiation treatment unit is disclosed. The method and system comprises relevant identifying information about the patient to a server and determining the disease of the patient to be treated. The method and system further includes providing the radiation treatment protocol based upon the patient information and the disease from the server to the treatment unit. Accordingly, through the present invention a treatment plan is provided based upon information in a database within the server. In addition, the database can be updated on a regular basis through access to the Internet, intranet, or other types of input to insure that the particular treatment plan provided is the most up-to-date treatment plan for the disease to be treated. In so doing, a system is provided that can be used in settings where experts are not available.

37 Claims, 6 Drawing Sheets

METHOD AND SYSTEM FOR PROVIDING RADIATION TREATMENT TO A PATIENT

FIELD OF THE INVENTION

The present invention relates to radiation therapy treatment and more particularly to a system and method for providing such treatment.

BACKGROUND OF THE INVENTION

Radiotherapy devices are generally used for the treatment of patients. A radiation therapy device usually comprises a gantry which can be swiveled around a horizontal axis of rotation in the course of a therapeutic treatment. A linear accelerator is located in the gantry for generating a high energy radiation beam for therapy. This high energy radiation beam can be an electron radiation or photon x-ray beam. During treatment, this radiation beam is trained on a zone of a patient lying on the isocenter of the gantry rotation. The delivery of radiation by a radiation therapy device is prescribed and approved by an oncologist. Actual operation of the radiation equipment, however, is normally done by a therapist. When the therapist administers the actual delivery of the radiation treatment as prescribed by the oncologist, the radiation emitting device is programmed to deliver the specific treatment.

Typically, in such a system, the oncologist has a clear understanding of the particular type of treatment that is desired. For example, if it is a prostate cancer treatment, the oncologist will be an expert in that type of cancer treatment and will provide the appropriate treatment plan. Similarly, if the cancer is a breast cancer, then the oncologist that has sufficient knowledge about that type of cancer will provide the treatment regarding that type of cancer. However, in those instances where an expert is not available, it is possible that the patient may not receive the kind of treatment that can aggressively treat a particular type of problem. Particularly in areas that are undeveloped, i.e., third world countries, where experts are not available, it would be desirable to be able to provide the best possible treatment plan for a particular type of cancer. Accordingly, what is desired is a system allowing for a radiation therapy treatment where an expert is not available to provide the particular treatment plan. The system should be easy to use, adaptable, and compatible with existing radiotherapy equipment. The present invention addresses such a need.

SUMMARY OF THE INVENTION

A method and system for providing a radiation treatment to a patient utilizing a radiation treatment is disclosed. The method and system comprises providing relevant identifying information about the patient to a server; and determining the disease of the patient to be treated. The method and system further includes providing a radiation treatment protocol based upon the patient information and the disease from the server to the treatment unit.

Accordingly, through the present invention a treatment plan is provided based upon information in a database within the server. In addition, the database can be updated on a regular basis through access to the Internet, intranet, or other types of input to insure that the particular treatment plan provided is the most up-to-date treatment plan for the disease to be treated. In so doing, a system is provided that can be used in settings where experts are not available.

DETAILED DESCRIPTION

The present invention relates to radiation therapy treatment and more particularly to a system and method for providing such treatment. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

Figure 1:
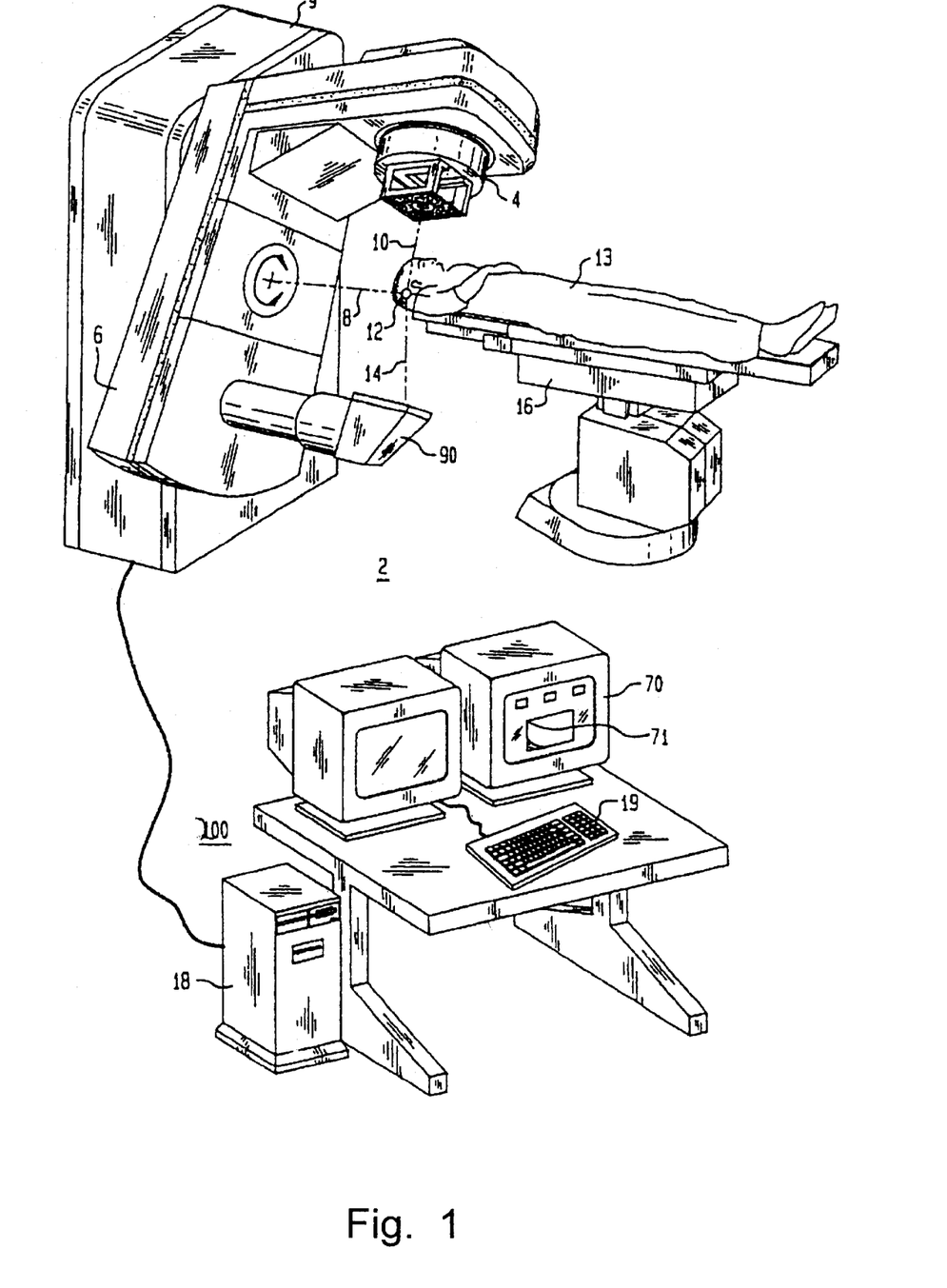
FIG. 1 is a radiation treatment apparatus in accordance with the present invention.

Turning now to the drawings and, with particular attention to FIG. 1, a radiation treatment apparatus embodying the present invention is shown therein and generally identified by reference numeral 2. The radiation treatment apparatus 2 is configured to vary the synchronization of the RF modulator pulse and the injector pulse, as will be discussed in greater detail below. The radiation treatment apparatus 2 includes a beam shielding device (not shown) within a treatment head 4, a control unit in a housing 9 and a treatment unit 200 according to the present invention. The radiation treatment device 2 includes a gantry 6 which can be swiveled around a horizontal axis of rotation 8 in the course of a therapeutic treatment. The treatment head 4 is fastened to the projection of the gantry 6. A linear accelerator is located in the gantry 6 to generate the high powered radiation required for the therapy. The axis of the radiation bundle emitted from the linear accelerator and the gantry 6 is designated by 10. Electron, photon or any other detectable radiation can be used for the therapy.

During the treatment, the radiation beam is trained on a zone 12 of an object 13, for example, a patient who is to be treated and who lies at the isocenter of the gantry rotation. The rotational axis 8 of the gantry 6, the rotational axis 14 of a treatment table 16, and the beam axis 10 intersect in the isocenter.

The plates or leaves of the beam shielding device within the treatment head 4 are substantially impervious to the emitted radiation. The collimator leaves or plates are mounted between the radiation source and the patient in order to delimit the field. Areas of the body, for example, healthy tissue, are therefore subject to as little radiation as possible and preferably to none at all. The plates or leaves are moveable such that the distribution of radiation over the field need not be uniform (one region can be given a higher dose than another). Furthermore, the gantry can be rotated so as to allow different beam angles and radiation distributions without having to move the patient.

The radiation treatment device 2 also includes a central treatment processing or control unit 200 which is typically located apart from the radiation treatment device 2. The radiation treatment device 2 is normally located in a different room to protect the therapist from radiation. The treatment unit 200 includes output devices such as at least one visual display unit or monitor 70 and an input device such as a keyboard 19. Data can be input also through data carriers such as data storage devices or a verification and recording or automatic setup system.

The treatment processing unit 200 is typically operated by the therapist who administers actual delivery of radiation treatment as prescribed by an oncologist by using the keyboard 19 or other input device. The therapist enters into the control unit of the treatment unit 200 the data that defines the radiation dose to be delivered to the patient, for example, according to the prescription of the oncologist. The program can also be input via another input device, such as a data storage device. Various data can be displayed before and during the treatment on the screen of the monitor 70.

Typically in this type of system, the oncologist will be an expert who has a full knowledge of how a treatment plan should be administered. However, in many instances the oncologist may not have the latest information regarding a particular treatment of a particular type of cancer. For example, if the patient is in an undeveloped country where there is not easy access to a physician or oncologist that has the requisite knowledge, the treatment provided by the oncologist might not be adequate or possible. Accordingly, a system and method in accordance with the present invention allows one to develop a treatment plan based on information retrieved from the treatment unit.

To more fully describe the features of the present invention, refer now to the following discussion in conjunction with the accompanying figures.

Figure 2:
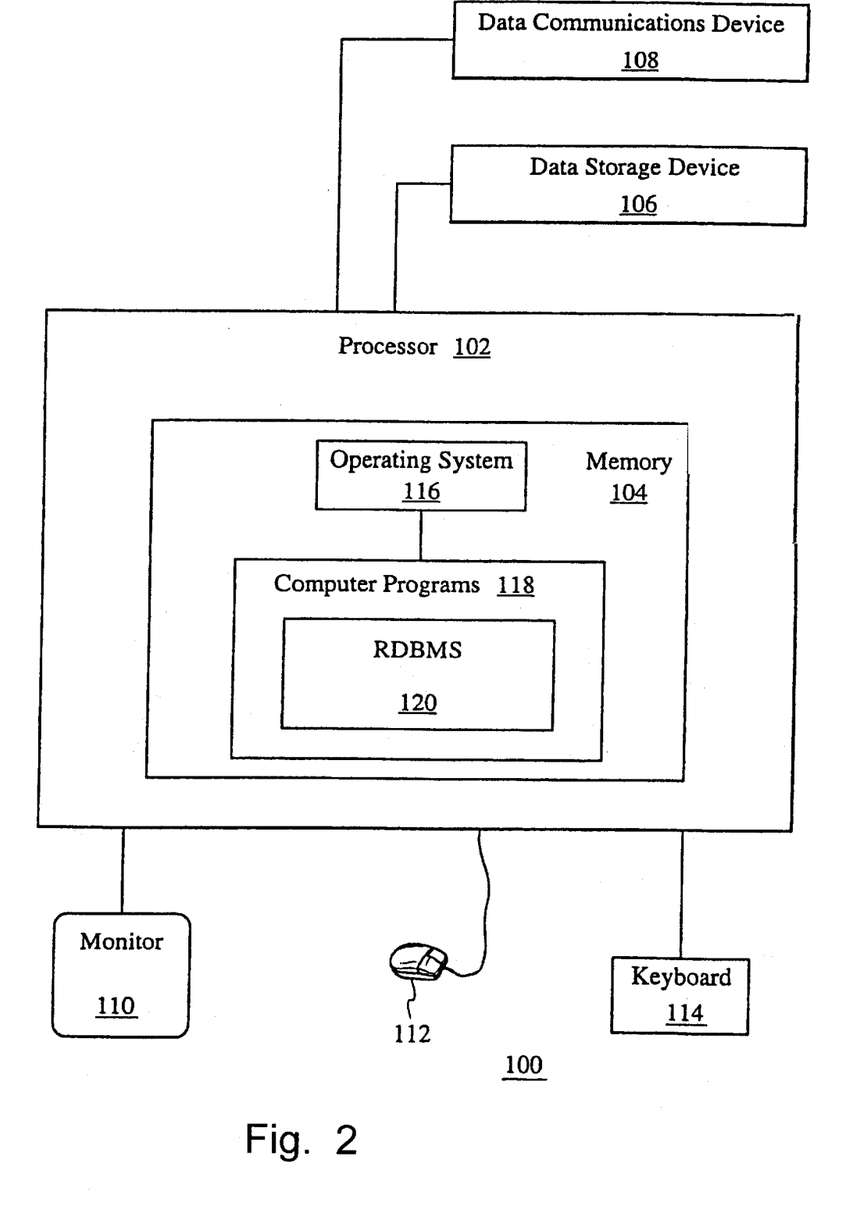
FIG. 2 illustrates a hardware environment used to implement the present invention.

Accordingly, FIG. 2 illustrates a hardware environment used to implement the present invention. As illustrated in FIG. 2, in the preferred embodiment the present invention is implemented in a server computer ("server") 100. The server 100 could be part of the treatment unit 200 (FIG. 1) or could be a separate unit. The server 100 generally includes, a processor 102, a memory 104 such as a random access memory (RAM), a data storage device 106 (e.g., hard drive, floppy disk drive, CD-ROM disk drive, etc.), a data communication device 108 (e.g., modem, network interface device, etc.), a monitor 110 (e.g., CRT, LCD display, etc.), a pointing device 112 (e.g., a mouse, a track ball, a pad or any other device responsive to touch, etc.) and a keyboard 114. It is envisioned that attached to the computer 100 may be other devices such as read only memory (ROM), a video card drive, printers, peripheral devices including local and wide area network interface devices, etc. One of ordinary skill in the art will recognize that any combination of the above system components may be used to configure the server 100.

The server 100 operates under the control of an operating system ("OS") 116, such as MVS™, AIX™, UNIX™, OS/2™, WINDOWS™, WINDOWS NT™, etc., which typically, is loaded into the memory 104 during the server 100 start-up (boot-up) sequence after power-on or reset. In operation, the OS 116 controls the execution by the server 100 of computer programs 118, including server and/or client-server programs. Alternatively, a system and method in accordance with the present invention may be implemented with any one or all of the computer programs 118 embedded in the OS 116 itself without departing from the scope of the invention. Preferably, however, the client programs are separate from the server programs and are not resident on the server.

The OS 116 and the computer programs 118 each comprise computer readable instructions which, in general, are tangibly embodied in or are readable from a media such as the memory 104, the data storage device 106 and/or the data communications device 108. When executed by the server 100, the instructions cause the server 100 to perform the steps necessary to implement the present invention. Thus, the present invention may be implemented as a method, apparatus, or an article of manufacture (a computer-readable media or device) using programming and/or engineering techniques to produce software, hardware, firmware, or any combination thereof.

The server 100 is typically used as a part of an information search and retrieval system capable of receiving, retrieving and/or disseminating information over the Internet, or any other network environment. One of ordinary skill in the art will recognize that this system may include more than one of server 100.

In the information search and retrieval system, such as a digital library system, a client program communicates with the server 100 by, inter alia, issuing to the server search requests and queries. The server 100 then responds by providing the requested information. The digital library system is typically implemented using a database management system software (DBMS) 120 such as the DB2™ by IBM Corporation. The DBMS 120 receives and responds to search and retrieval requests and termed queries from the client. In the preferred embodiment, the DBMS 120 is server-resident.

Objects are typically stored in a relational database connected to an object server, and the information about the objects is stored in a relational database connected to a library server, wherein the server program(s) operate in conjunction with the (DBMS) 120 to first store the objects and then to retrieve the objects. One of ordinary skill in the art will recognize that the foregoing is an exemplary configuration of a system which embodies the present invention, and that other system configurations may be used without departing from the scope and spirit of the present invention.

Accordingly, a system and method in accordance with the present invention allows for the appropriate treatment plan to be provided via the server based on information within the server or accessed by the server. To more fully describe this feature, refer now to FIG. 3.

Figure 3:
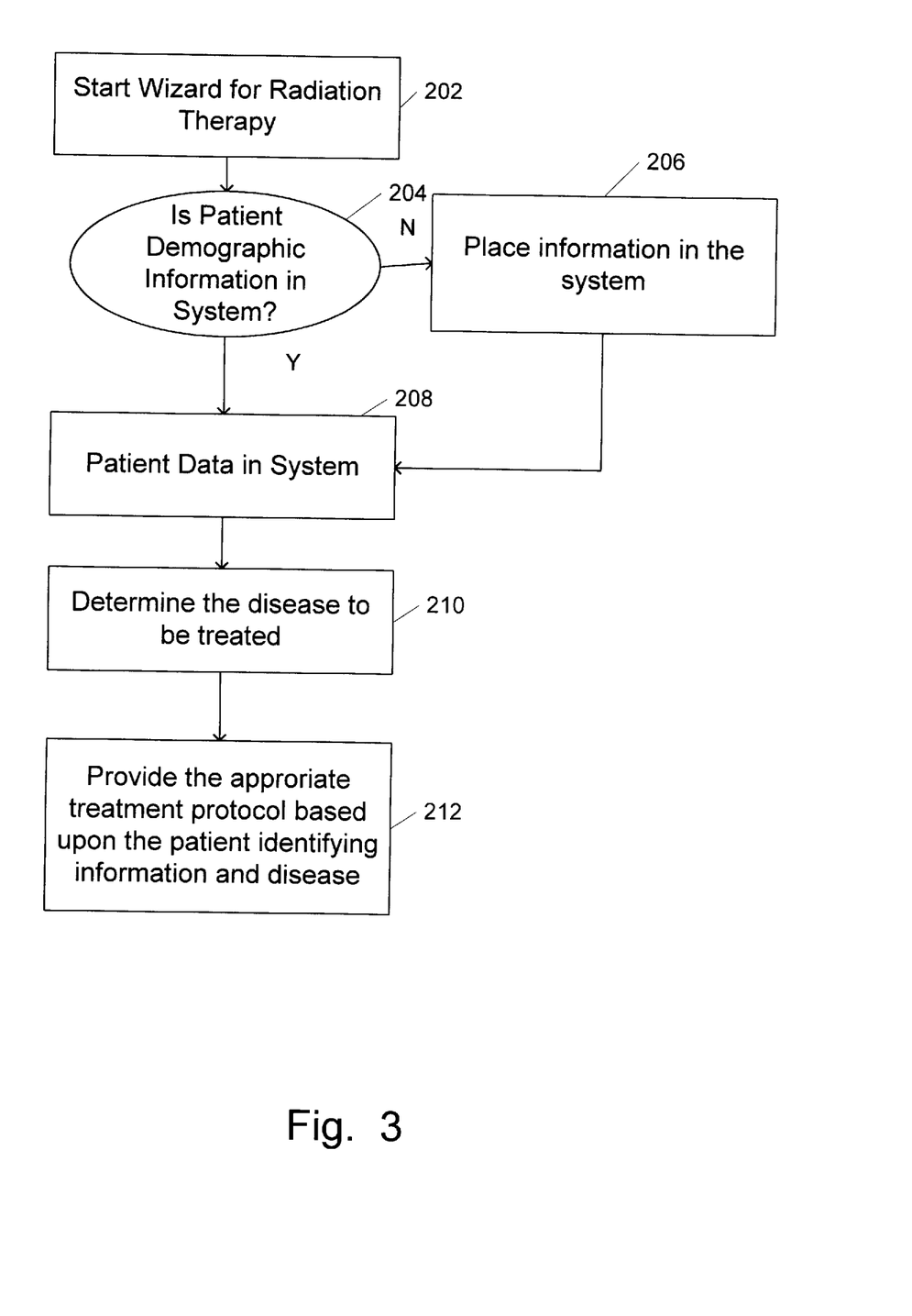
FIG. 3 is a flow chart illustrating a system and method in accordance with the present invention.

FIG. 3 is a flow chart illustrating a system and method in accordance with the present invention. In a preferred embodiment, a treatment wizard would be initiated for radiation therapy, via step 202. Next, it is determined if demographic information is within the system, via step 204. If there is no patient demographic information in the system, then the data must be entered into the system, via step 206. The information can be placed in the system either via a manual entry or via an electronic patient record system, via step 208. Next, it is determined what disease needs to be treated, via step 210. The appropriate treatment protocol is then provided, based upon the patient identifying information and the disease to be treated, via step 212

The appropriate treatment protocol could be implemented in a variety of ways depending upon the protocol used. For example, Siemens Corporation provides treatment protocols from its centers of excellence (COE) for a variety of diseases (such as prostate cancer, breast cancer, head and neck cancer, etc.) To illustrate the treatment protocol providing step 212 in more detail, refer now to the following discussion conjunction with the accompanying figure.

Figure 4:
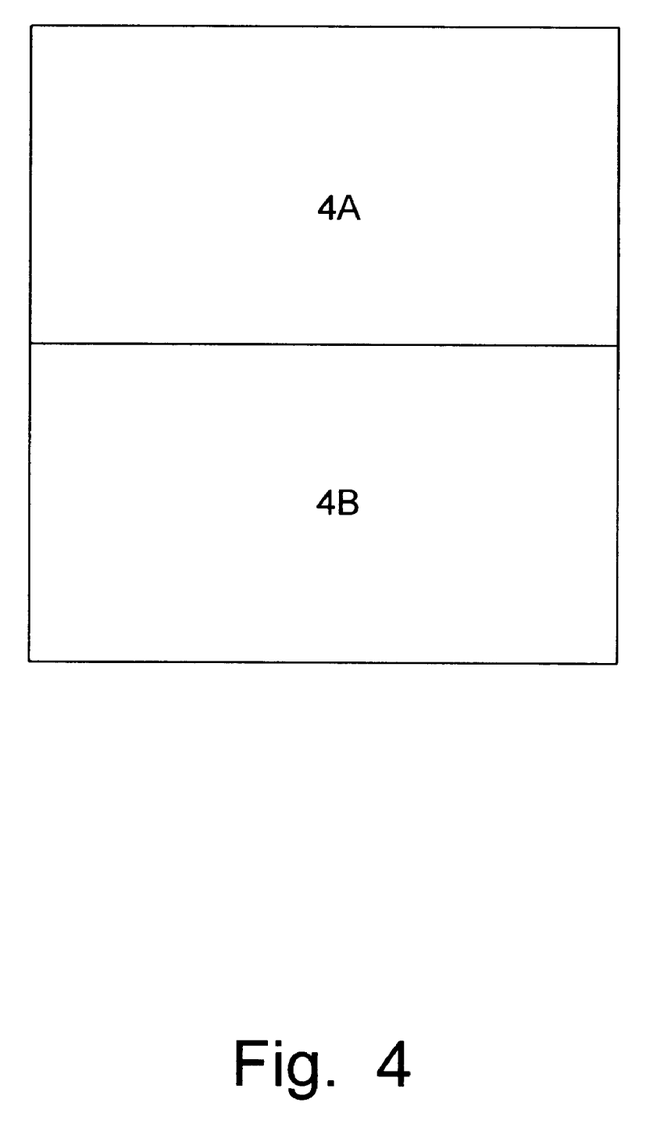
FIGS. 4, 4a, and 4b are a flow chart which illustrates providing the appropriate treatment protocol in accordance with the present invention.
Figure 4A:
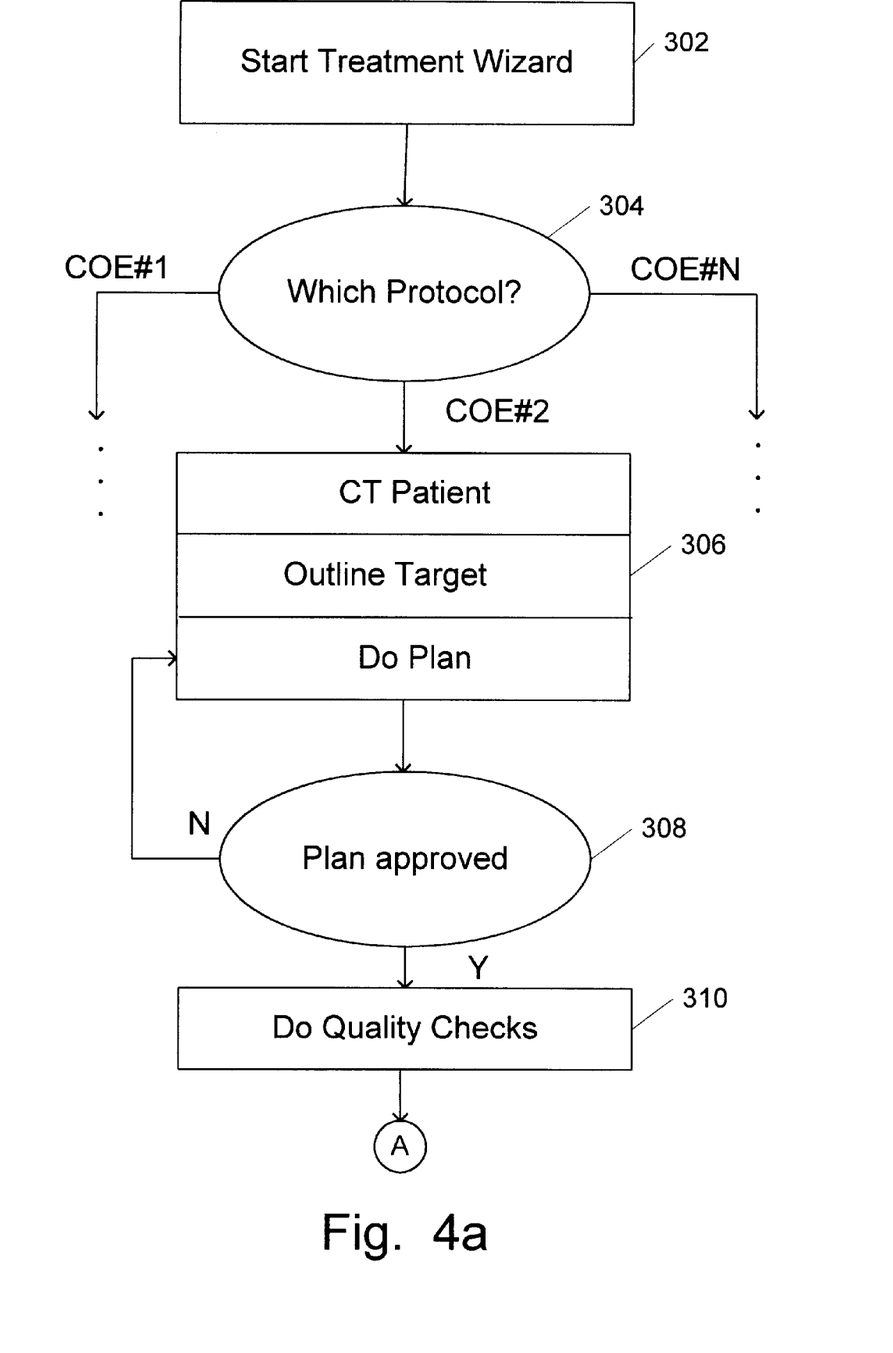
Figure 4B:
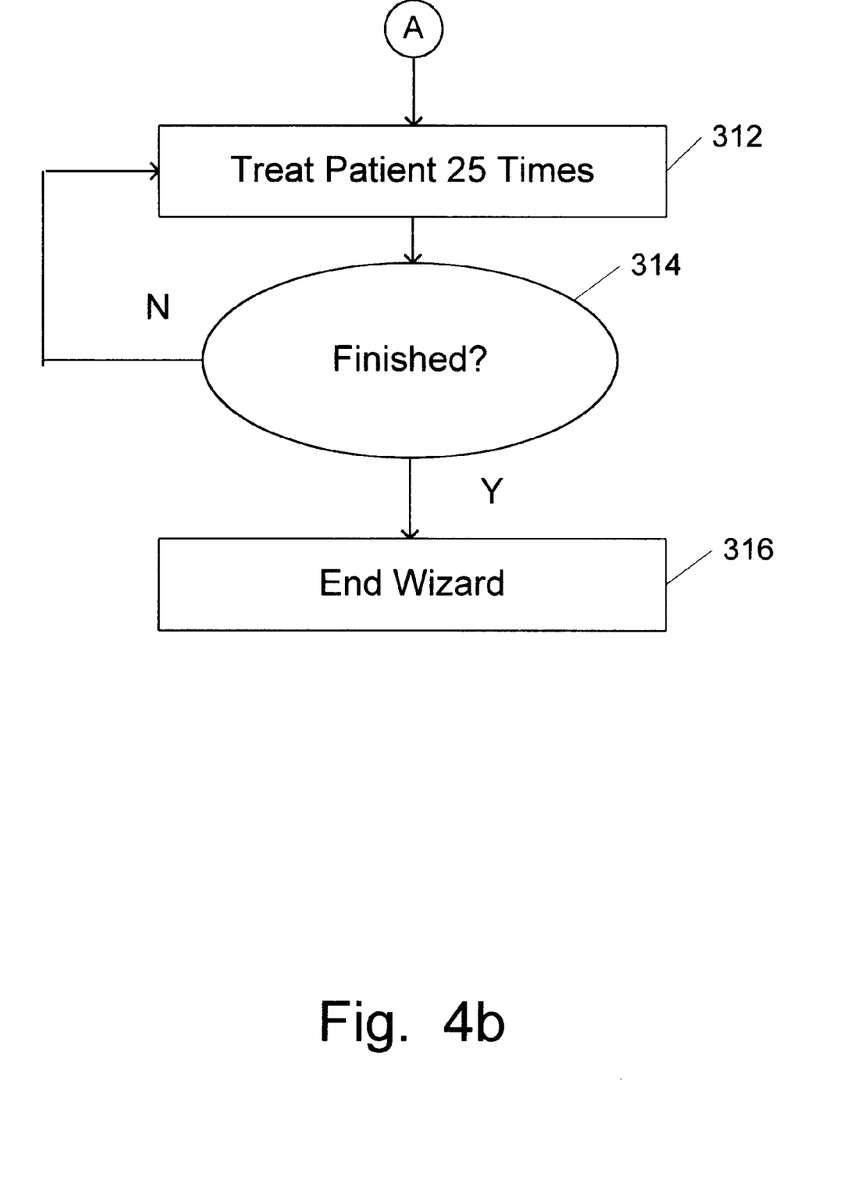

FIG. 4 is a flow chart which illustrates providing the appropriate treatment protocol in accordance with the present invention. First a wizard is initiated for treating a particular disease (for example, prostate cancer), via step 302. Next, a determination is made as to which protocol will be provided, via step 304. Any number of protocols (COE#1–COE#n) could be provided based upon the COE's capability. In the case of a prostate cancer treatment, a CT of the patient will be taken, the target tumors will then be outlined and a treatment plan will be provided, via step 306. Next, it will be determined if the plan has been approved, via step 308. If the plan has not been approved, then a new plan is provided, via step 306. Once the plan is approved, then quality checks are performed, via step 310.

Next, the target is treated a predetermined number of times (for example, 25 times), via step 312. Steps 306 and 312 are duplicated from the appropriate COE protocol to provide the patient with the most effective treatment. Accordingly, the user of the system does not have to be an expert in the field to provide this treatment based upon the COE. Thereafter, a determination is made whether the treatment is finished, via step 314. If the treatment is not finished, return to step 312. If the treatment is finished, then end treatment wizard.

Accordingly, through the present invention a treatment plan could be provided based upon a protocol in a database within the server. In addition, the database can be updated on a regular basis through access to the Internet, intranet, or other types of input to insure that the particular treatment plan provided is the most up-to-date treatment plan for the disease to be treated. In so doing, a system is provided that can be used in settings where experts are not available.

In a preferred embodiment, the treatment plan is implemented by a "wizard" which would allow the user to input information in response to queries via the user interface to provide the optimum treatment. A system and method in accordance with the present invention could allow for certain queries to provide access to a private network, public network, or intranet which could provide access to additional information that would improve the treatment plan.

Therefore, better treatment can be provided in those situations which will enhance the quality of care for a particular patient. This system could be utilized with any type of radiation therapy treatment, including prostate cancer, breast cancer, and any other types of radiation treatment plans to insure that the patient receives the optimum care. Accordingly, what is provided is a system and method for improving the care for an individual when receiving radiation treatment. Through the ability to obtain the most current information about treating a particular type of disease, it is possible for an individual, where an expert is not available, to provide a high quality of care through access to such information. The system can be easily implemented on existing equipment and it is cost-effective and relatively inexpensive to implement.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A method for providing a radiation treatment to a patient utilizing a radiation treatment unit, the method comprising the steps of:
   (a) providing relevant identifying information about the patient to a server;
   (b) determining the disease of the patient to be treated; and
   (c) providing the radiation treatment protocol based upon the patient information and the disease from the server to the treatment unit.

2. The method of claim 1 wherein the radiation treatment protocol is provided via a wizard.

3. The method of claim 1 wherein the radiation treatment providing step (c) comprises the steps of:
   (c1) determining the protocol to be provided; and
   (c2) providing a treatment plan based upon the protocol.

4. The method of claim 3 wherein the treatment plan providing (306) step (c2) comprises:
   (c21) determining if the treatment plan has been approved, and
   (c22) performing quality checks if the treatment plan is approved.

5. The method of claim 4 which includes the step (d) of administering and radiation treatment based upon the radiation treatment protocol.

6. The method of claim 5 wherein the administering step (d) comprises the step (d1) of treating the patient a predetermined number of times.

7. The method of claim 1 wherein the server can access a network.

8. The method of claim 7 wherein the network comprises a public network.

9. The method of claim 7 wherein the network comprises a private network.

10. A system for providing a radiation treatment to a patient utilizing a
    radiation treatment unit, the system comprising:
        means for providing relevant identifying information about the patient to a server;
        means for determining the disease of the patient to be treated; and
        means for providing the radiation treatment protocol based upon the patient information and the disease from the server to the treatment unit.

11. The system of claim 10 wherein the radiation treatment protocol is provided via a wizard.

12. The system of claim 10 wherein the radiation treatment providing means comprises:
    means for determining the protocol to be provided; and
    means for providing a treatment plan based upon the protocol.

13. The system of claim 12 wherein the treatment plan providing means comprises:
    means for determining if the treatment plan has been approved, and
    means for performing quality checks if the treatment plan is approved.

14. The system of claim 13 which includes means for administering radiation treatment based upon the radiation treatment protocol.

15. The system of claim 14 wherein the administering means comprises the means for treating the patient a predetermined number of times.

16. The system of claim 10 wherein the server can access a network.

17. The system of claim 16 wherein the network comprises a public network.

18. The system of claim 16 wherein the network comprises a private network.

19. A computer readable medium containing program instructions for providing a radiation treatment to a patient utilizing a radiation treatment unit, the program instructions for:

(a) providing relevant identifying information about the patient to a server;

(b) determining the disease of the patient to be treated; and (c) providing the radiation treatment protocol based upon the patient information and the disease from the server to the treatment unit.

20. The computer readable medium of claim 19 wherein the radiation treatment protocol is provided via a wizard.

21. The computer readable medium of claim 19 wherein the radiation treatment providing step (c) comprises the steps of:

(c1) determining the protocol to be provided; and (c2) providing a treatment plan based upon the protocol.

22. The computer readable medium of claim 21 wherein the treatment plan providing step (c2) comprises:

(c21) determining if the treatment plan has been approved, and (c22) performing quality checks if the treatment plan is approved.

23. The computer readable medium of claim 22 which includes program instructions for (d) administering radiation treatment based upon the radiation treatment protocol.

24. The computer readable medium of claim 23 wherein the administering step (d) comprises the step (d1) of treating the patient a predetermined number of times.

25. The computer readable medium of claim 19 wherein the server can access a network.

26. The computer readable medium of claim 25 wherein the network comprises a public network.

27. The computer readable medium of claim 25 wherein the network comprises a private network.

28. A system for providing a radiation treatment to a patient, the system comprising:

a radiation treatment unit (2); and a server coupled to the radiation treatment unit (2), the server for receiving relevant identifying information about the patient; and providing a radiation treatment protocol based upon the patient information and the disease.

29. The system of claim 28 wherein the radiation treatment protocol is provided via a wizard (202).

30. The system of claim 28 wherein the server (100) includes:

means for determining the protocol to be provided; and means for providing a treatment plan based upon the protocol.

31. The system of claim 29 wherein the treatment plan providing means comprises:

means for determining if the treatment plan has been approved, and means for performing quality checks if the treatment plan is approved.

32. The system of claim 31 which includes means for administering radiation treatment based upon the radiation treatment protocol.

33. The system of claim 32 wherein the administering means comprises the means for treating the patient a predetermined number of times.

34. The system of claim 28 wherein the server can access a network.

35. The system of claim 34 wherein the network comprises a public network.

36. The system of claim 34 wherein the network comprises a private network.

37. The system of claim 34 wherein the server includes a database, the database including information related to the treatment plan.

* * * * *